US010864918B2

(12) United States Patent
An

(10) Patent No.: US 10,864,918 B2
(45) Date of Patent: Dec. 15, 2020

(54) VEHICLE AND METHOD FOR SUPPORTING DRIVING SAFETY THEREOF

(71) Applicants: Hyundai Motor Company, Seoul (KR); Kia Motors Corporation, Seoul (KR)

(72) Inventor: Dae Yun An, Gyeonggi-do (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 259 days.

(21) Appl. No.: 16/025,096

(22) Filed: Jul. 2, 2018

(65) Prior Publication Data
US 2019/0161091 A1    May 30, 2019

(30) Foreign Application Priority Data
Nov. 28, 2017  (KR) .................. 10-2017-0160394

(51) Int. Cl.
*B60W 50/08*         (2020.01)
*B60W 50/14*         (2020.01)
(Continued)

(52) U.S. Cl.
CPC ....... *B60W 50/085* (2013.01); *A61B 5/04845* (2013.01); *A61B 5/18* (2013.01);
(Continued)

(58) Field of Classification Search
CPC .. B60W 50/085; B60W 30/182; B60W 40/08; B60W 50/14; B60W 2040/0827; B60W 2040/0845; B60W 2040/0818; B60W 2040/0836; B60W 2040/0872; B60W 2050/0071; B60W 2050/0095;
(Continued)

(56) References Cited

U.S. PATENT DOCUMENTS

| | | | |
|---|---|---|---|
| 8,239,015 B2 * | 8/2012 | Morikawa et al. | .... A61B 5/048 600/545 |
| 9,031,729 B2 | 5/2015 | Lathrop et al. | |

(Continued)

FOREIGN PATENT DOCUMENTS

| | | |
|---|---|---|
| JP | H11185200 A | 7/1999 |
| KR | 20160050444 A | 5/2016 |

(Continued)

OTHER PUBLICATIONS

Espacenet translation of WO2014092494A1, Method and Apparatus for Controlling Travelling Object Using Brain Waves, Kim et al, WIPO/PCT Publication, 12 pages (Year: 2014).*

*Primary Examiner* — Dale W Hilgendorf
(74) *Attorney, Agent, or Firm* — Mintz Levin Cohn Ferris Glovsky and Popeo, P.C.; Peter F. Corless

(57) ABSTRACT

A method for adjusting a driving control authority of a vehicle includes: generating stimulation for a driver using a stimulation generator; measuring a driver reaction signal in response to the generated stimulation using a measurement device; processing the measured driver reaction signal using a signal processor; determining a driver state based on the processed driver reaction signal using a determiner; and adjusting the driving control authority of the vehicle according to the determined driver state using a vehicle controller.

13 Claims, 11 Drawing Sheets

(51) Int. Cl.
  *G05D 1/00* (2006.01)
  *A61B 5/18* (2006.01)
  *A61B 5/0484* (2006.01)
  *A61B 5/00* (2006.01)
  *B60W 40/08* (2012.01)
  *B60K 28/06* (2006.01)
  *B60W 30/182* (2020.01)
  *A61B 5/16* (2006.01)
  *B60W 50/00* (2006.01)

(52) U.S. Cl.
  CPC .......... *A61B 5/6803* (2013.01); *A61B 5/7267* (2013.01); *B60K 28/06* (2013.01); *B60W 30/182* (2013.01); *B60W 40/08* (2013.01); *B60W 50/14* (2013.01); *G05D 1/0061* (2013.01); *A61B 5/04842* (2013.01); *A61B 5/162* (2013.01); *A61B 5/163* (2017.08); *B60W 2040/0818* (2013.01); *B60W 2040/0827* (2013.01); *B60W 2040/0836* (2013.01); *B60W 2040/0845* (2013.01); *B60W 2040/0872* (2013.01); *B60W 2050/0071* (2013.01); *B60W 2050/0095* (2013.01); *B60Y 2302/05* (2013.01); *G05D 2201/0213* (2013.01)

(58) Field of Classification Search
  CPC ................. B60K 28/06; G05D 1/0061; G05D 2201/0213; A61B 5/18; A61B 5/04845; A61B 5/6803; A61B 5/7267; A61B 5/163; A61B 5/162; A61B 5/04842; B60Y 2302/05
  See application file for complete search history.

(56) References Cited

U.S. PATENT DOCUMENTS

| | | | |
|---|---|---|---|
| 2011/0279676 A1* | 11/2011 | Terada et al. | A61B 5/18 348/148 |
| 2016/0282940 A1 | 9/2016 | Hong et al. | |
| 2017/0303842 A1* | 10/2017 | Yoshida et al. | B60W 30/182 |

FOREIGN PATENT DOCUMENTS

| | | | |
|---|---|---|---|
| KR | 101648017 B1 | 8/2016 | |
| WO | WO2014092494 A1 * | 6/2014 | A61B 5/18 |

* cited by examiner

VEHICLE AND METHOD FOR SUPPORTING DRIVING SAFETY THEREOF

CROSS-REFERENCE TO RELATED APPLICATION

This application claims the benefit of priority to Korean Patent Application No. 10-2017-0160394, filed on Nov. 28, 2017 in the Korean Intellectual Property Office, the disclosure of which is incorporated herein in its entirety by reference.

TECHNICAL FIELD

The present disclosure relates to a system and a method for controlling driving control authority of a vehicle, and more particularly, to a system and a method for controlling driving control authority of a vehicle by determining a bio-signal of a driver.

BACKGROUND

According to recent statistics, about 75% of road traffic accidents are caused due to driver error. For instance, the driver may fail to accurately evaluate the surrounding environment or the reaction of the driver may be delayed. To prevent such accidents, a technical means may be employed to inspect whether a driving state of the driver is safe.

A state of the driver may be determined based on physiological characteristics, such as fatigue, and psychological reaction time based on stimulation-reaction monitoring.

The inspection of driver fatigue may be performed by collecting and analyzing facial images of the driver (e.g., using a camera). In addition, a driving state of the driver can be inspected by identifying an occurrence of abnormal passing of the vehicle.

Psychological reaction monitoring based on stimulation-reaction monitoring can be performed to estimate the psychological reaction of the driver using a specific stimulation mode. For example, upon generating an artificial visible stimulation, the driver's eyes can be monitored to detect whether the driver pays attention to the stimulation in order to determine whether the driver has the ability to react to a currently occurring accident.

Accordingly, it would be beneficial to control a vehicle operation, such as driving of the vehicle, based on a driver state recognized through any of the above-described techniques or a similar manner.

SUMMARY

The present disclosure has been made to solve the above-mentioned problems occurring in the related art while advantages achieved by the prior art are maintained intact.

An aspect of the present disclosure provides a system and a method for adjusting driving control authority of a vehicle, capable of preventing a driver from performing the driving control under an emergency situation by adjusting the driving control authority of the vehicle depending on a recognized driver state.

The technical problems to be solved by the present disclosure are not limited to the aforementioned problems, and any other technical problems not mentioned herein will be clearly understood from the following description by those skilled in the art to which the present disclosure pertains.

According to embodiments of the present disclosure, a method for adjusting a driving control authority of a vehicle includes: generating stimulation for a driver using a stimulation generator; measuring a driver reaction signal in response to the generated stimulation using a measurement device; processing the measured driver reaction signal using a signal processor; determining a driver state based on the processed driver reaction signal using a determiner; and adjusting the driving control authority of the vehicle according to the determined driver state using a vehicle controller.

The generating of the stimulation may include generating auditory stimulation when the driver boards the vehicle.

The measuring of the driver reaction signal may include measuring a brainwave of the driver.

The processing of the driver reaction signal may include: performing filtering on the driver reaction signal to classify a signal other than the brainwave as noise; and extracting an event-related potential (ERP) from the filtered driver reaction signal.

The method may further include extracting, from the ERP, a potential having a maximum amplitude value after a specific time elapses from a time at which the auditory stimulation is generated.

The measuring of the driver reaction signal may include measuring a bio-signal of the driver.

The measuring of the driver reaction signal may further include measuring one of a heart rate of the driver and gaze information of the driver.

The determining of the driver state may include determining the driver state to be a normal state when a maximum amplitude value of the brainwave is greater than or equal to a reference value.

The adjusting of the driving control may include controlling operation of the vehicle such that the vehicle performs either autonomous driving or manual driving when the driver state is the normal state.

The determining of the driver state may include determining the driver state to be an abnormal state when a maximum amplitude value of the brainwave is less than a reference value.

The adjusting of the driving control authority of the vehicle may include controlling operation of the vehicle such that the vehicle performs either autonomous driving or an emergency stop when the driver state is the abnormal state.

Furthermore, according to embodiments of the present disclosure, a system for adjusting a driving control authority of a vehicle includes: a stimulation generator to generate stimulation for a driver; a measurement device including a sensor device configured to measure a driver reaction signal in response to the generated stimulation; a signal processor configured to process the measured driver reaction signal; a determiner configured to determine a driver state based on the processed driver reaction signal; and a vehicle controller configured to adjust the driving control authority of the vehicle according to the determined driver state.

The stimulation generator may generate the auditory stimulation when a driver boards the vehicle.

The sensor device may be included in the vehicle or wearable by the driver.

The driver reaction signal may include a brainwave of a driver.

The signal processor may include: a filter configured to classify a signal of the driver reaction signal other than a brainwave signal as noise; and a feature point extractor configured to extract an ERP from the filtered driver reaction signal.

The determiner may determine the driver state to be the normal state when a maximum amplitude value of a brainwave is greater than or equal to a reference value.

The vehicle controller may control operation of the vehicle such that the vehicle performs autonomous driving or manual driving when the driver state is the normal state.

The determiner may determine the driver state to be the abnormal state when a maximum amplitude value of a brainwave is less than a reference value.

The vehicle controller may control operation of the vehicle such that the vehicle performs either autonomous driving or an emergency stop when the driver state is the abnormal state.

BRIEF DESCRIPTION OF THE DRAWINGS

The above and other objects, features and advantages of the present disclosure will be more apparent from the following detailed description taken in conjunction with the accompanying drawings.

Figure 1:
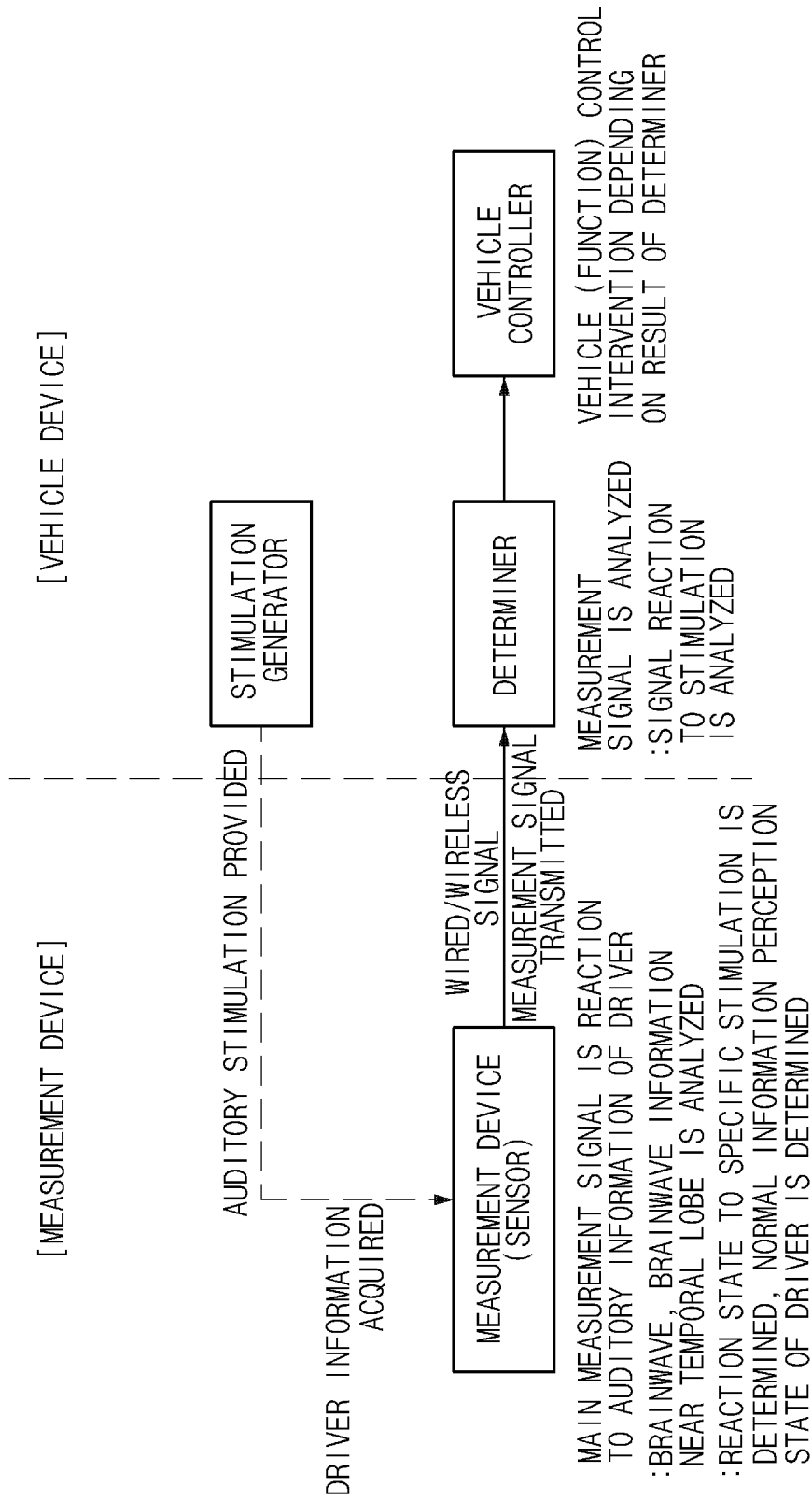
FIG. 1 is a schematic view illustrating a vehicle system to adjust driving control authority, according to embodiments of the present disclosure.

It should be understood that the above-referenced drawings are not necessarily to scale, presenting a somewhat simplified representation of various preferred features illustrative of the basic principles of the disclosure. The specific design features of the present disclosure, including, for example, specific dimensions, orientations, locations, and shapes, will be determined in part by the particular intended application and use environment.

DETAILED DESCRIPTION OF THE EMBODIMENTS

Hereinafter, embodiments of the present disclosure will be described in detail with reference to accompanying drawings. In the following description, the same reference numerals will be assigned to the same elements even though the elements are illustrated in different drawings. In addition, in the following description, a detailed description of well-known features or functions will be ruled out in order not to unnecessarily obscure the gist of the present disclosure.

The terminology used herein is for the purpose of describing particular embodiments only and is not intended to be limiting of the disclosure. In the following description of elements according to an embodiment of the present disclosure, the terms 'first', 'second', 'A', 'B', '(a)', and '(b)' may be used. The terms are used only to distinguish relevant elements from other elements, and the nature, the order, or the sequence of the relevant elements is not limited to the terms. In addition, unless otherwise defined, all terms used herein, including technical or scientific terms, have the same meanings as those generally understood by those skilled in the art to which the present disclosure pertains. Such terms as those defined in a generally used dictionary are to be interpreted as having meanings equal to the contextual meanings in the relevant field of art, and are not to be interpreted as having ideal or excessively formal meanings unless clearly defined as having such in the present application.

As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g., fuels derived from resources other than petroleum). As referred to herein, a hybrid vehicle is a vehicle that has two or more sources of power, for example both gasoline-powered and electric-powered vehicles.

Additionally, it is understood that one or more of the below methods, or aspects thereof, may be executed by at least one vehicle controller. The term "vehicle controller" may refer to a hardware device that includes a memory and a processor. The memory is configured to store program instructions, and the processor is specifically programmed to execute the program instructions to perform one or more processes which are described further below. Moreover, it is understood that the below methods may be executed by an apparatus comprising the vehicle controller in conjunction with one or more other components, as would be appreciated by a person of ordinary skill in the art.

Referring now to the presently disclosed embodiments, FIG. 1 is a schematic view illustrating a vehicle system to adjust driving control authority, according to embodiments of the present disclosure.

As illustrated in FIG. 1, in the vehicle system which adjusts the driving control authority according to embodiments of the present disclosure, a sensor of a measuring device measures a reaction signal (alternatively referred to herein as a "driver reaction signal") in response to stimulation generated from a stimulation generator of a vehicle. The reaction signal to auditory information generated from the vehicle may be measured using brainwave information near the temporal lobe. Alternatively, the reaction signal may be measured using brainwave information near the frontal lobe, middle lobe, or occipital lobe, as well as the temporal lobe.

According to embodiments of the present disclosure, an event related potential (ERP) is extracted by processing the measured reaction signal and the determiner determines a driver state using a potential from the ERP, which has the maximum amplitude value after a specific time elapses from a time in which the stimulation is generated from the vehicle. In this case, the potential having the maximum amplitude value has different values in the cases that the driver states are the normal and abnormal states. Accordingly, if the maximum amplitude value is greater than or equal to the reference value, the driver state is determined to be the normal state. If the maximum amplitude value is less than the reference value, the driver state is determined to be the abnormal state.

A vehicle controller may adjust the driving control authority of the vehicle depending on the result of the determiner. If the driver state is determined to be the normal state, the vehicle controller may control operation of the vehicle such that the vehicle performs any one of autonomous driving and manual driving. If the driver state is determined to be the abnormal state, the vehicle controller may adjust the driving control authority of the vehicle to perform any one of autonomous driving or emergency stop. Although the above description has been briefly made with reference to FIG. 1 regarding the vehicle system which adjusts the driving control authority according to the present disclosure, the vehicle system will be described in more detail with reference to FIG. 2.

Figure 2:
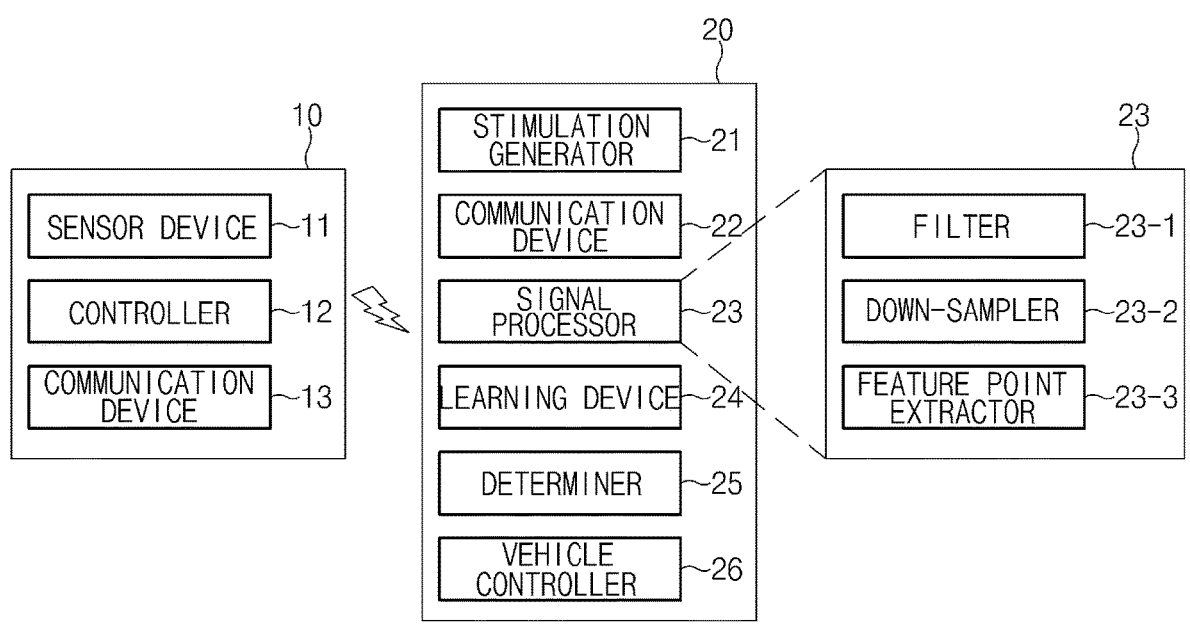
FIG. 2 is a block diagram illustrating the vehicle system to adjust the driving control authority, according to embodiments of the present disclosure.

FIG. 2 is a block diagram illustrating the vehicle system which adjusts the driving control authority according to embodiments of the present disclosure.

As illustrated in FIG. 2, the vehicle system which adjusts the driving control authority according to embodiments of the present disclosure may include a measurement device 10 and a vehicle 20.

The measurement device 10 may include a sensor device 11, a controller 12, and a communication device 13. Although FIG. 2 illustrates that the measurement device 10 wirelessly communicates with the vehicle 20 for the convenience of explanation, the present disclosure is not limited thereto. For example, the measurement device 10 may be included in the vehicle 20. The measurement device 10 may measure the reaction of a driver to the auditory information according to embodiments of the present disclosure. In more detail, the measurement device 10 may measure brainwave information near the temporal lobe to determine the reaction state to specific stimulation, thereby determining whether the driver normally recognizes information.

Figure 3:
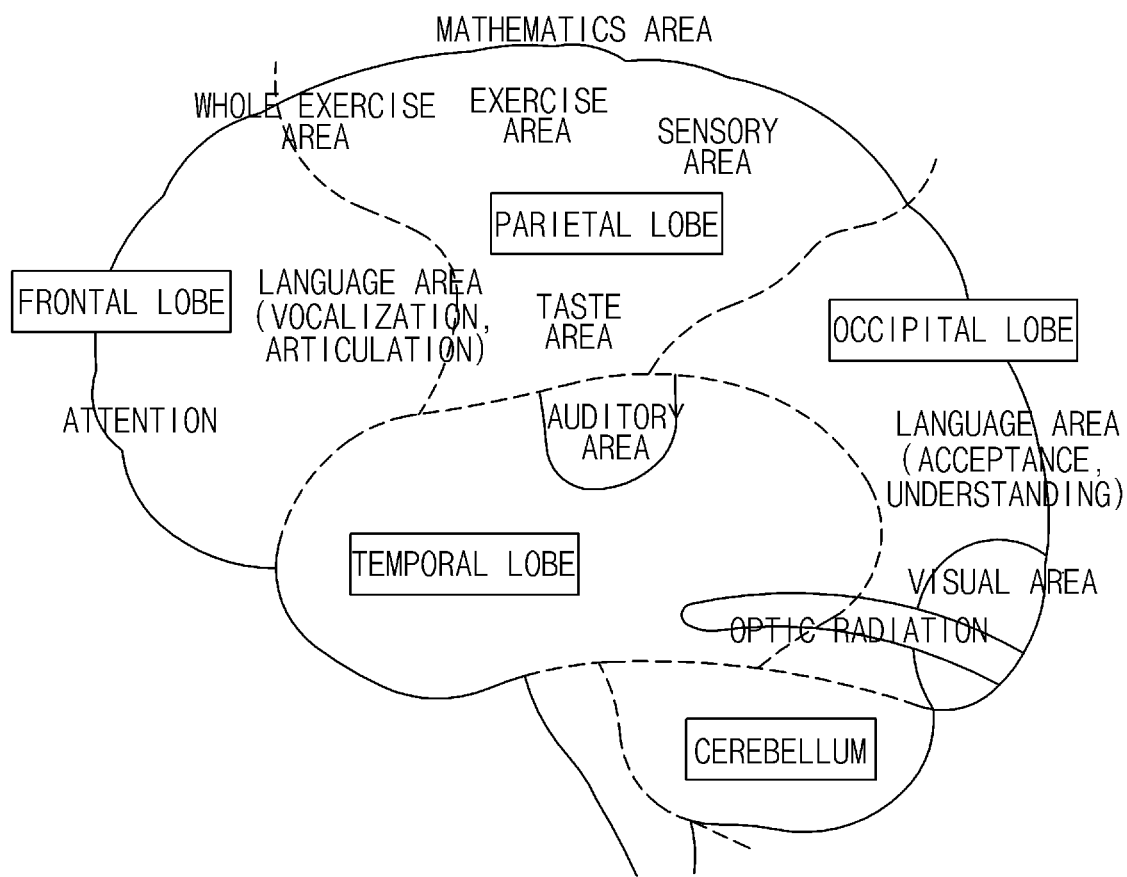
FIG. 3 is a view illustrating a position, at which a brainwave signal measured by a sensor device is generated, according to embodiments of the present disclosure.
Figure 4:
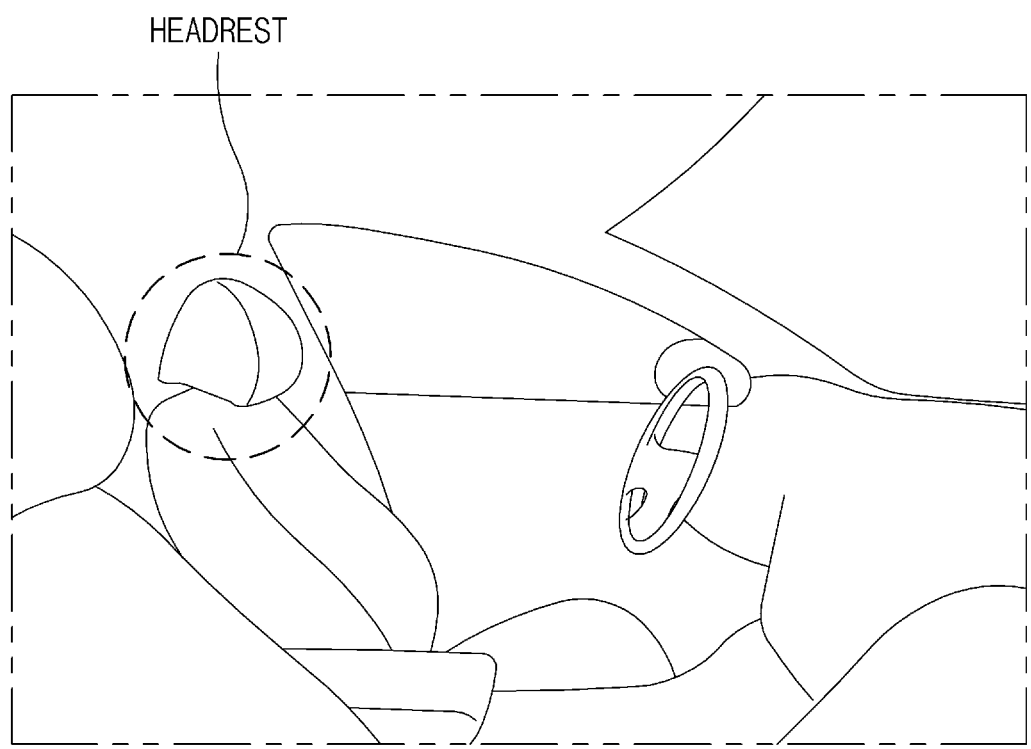
FIGS. 4 to 7 are views illustrating devices having the sensor device, according to embodiments of the present disclosure.

The sensor device 11 measure a reaction signal which reacts to stimulation (e.g., auditory stimulation) provided by the vehicle. The sensor device 11 may measure the reaction signal at the frontal lobe, the temporal lobe, the middle lobe, or the occipital lobe as illustrated in FIG. 3. In more detail, according to the present disclosure, the reaction signal to the stimulation may be measured by using the brainwave of the driver. To this end, according to embodiments of the present disclosure, the sensor device 11 may be mounted in a headrest inside the vehicle, as illustrated in FIG. 4. If proximity measurement is necessary, a sensor projects and directly or indirectly makes contact with a peripheral part of the temporal lobe to measure the brainwave.

For reference, the brainwave of a person may be acquired from an event related potential (ERP), a steady state visually evoked potential (SSVEP), an event related synchronization (ERS), an event related desynchronization (ERD), a default mode network, or the combination thereof.

Figure 5:
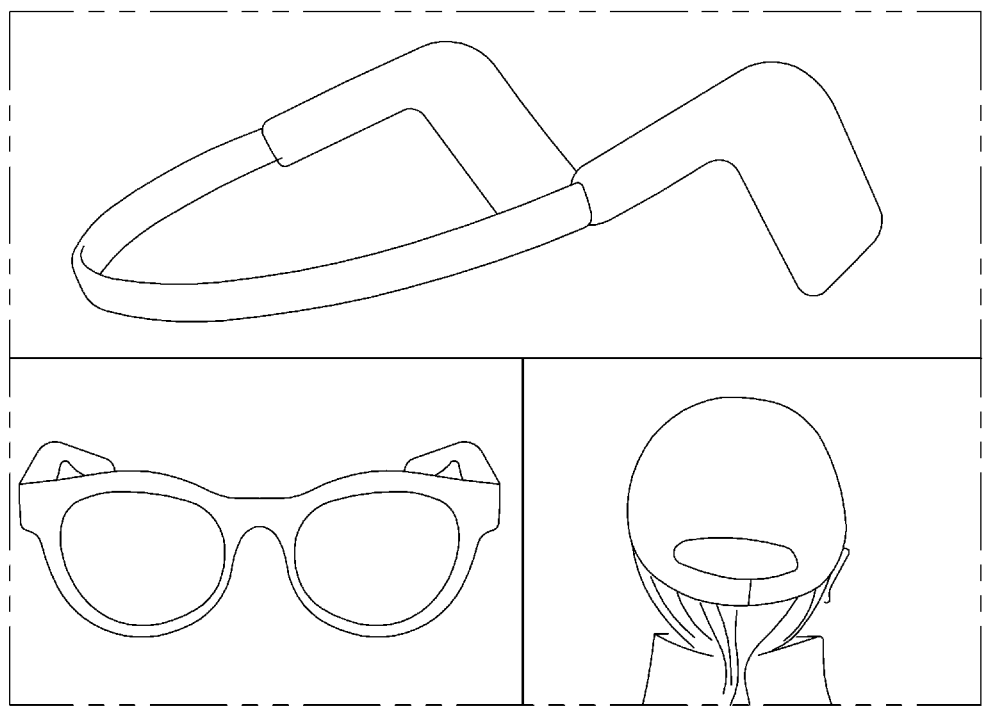
Figure 6:
Figure 7:
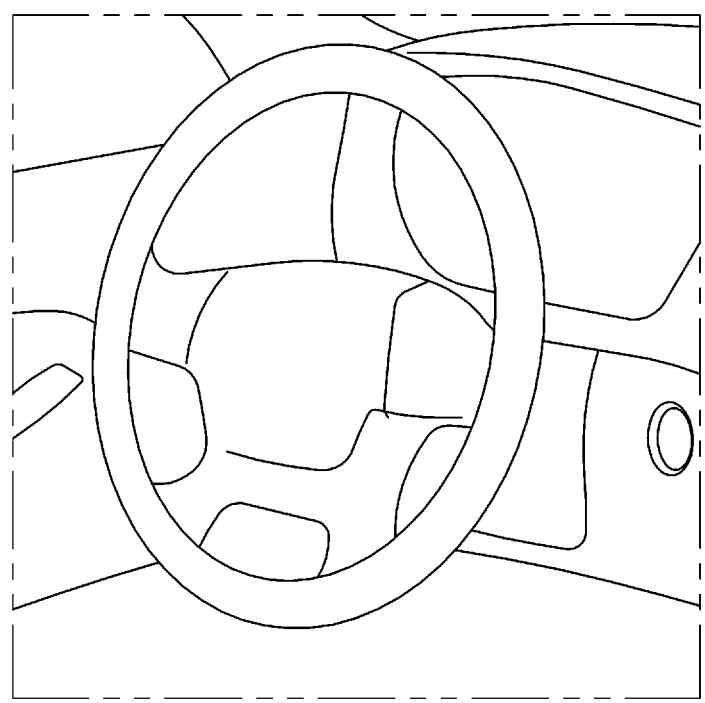

According to another example, the sensor device 11 may be provided in one of a headset type or a hairband type, as illustrated in FIG. 5. In addition, the sensor device 11 may be embedded in glasses, a headphone, or a cap, which is able to directly make contact with the human body, and the driver may put on the sensor device 11. The sensor device 11 is not limited to the above-described embodiment, and may be included in a wearable device which minimizes the restriction to the driver. Further, various bio-signal information may be used to react to a stimulation (e.g., visible or auditory stimulation) provided by the vehicle. For example, the bio-signal information may include a hear rate of the driver or gaze information (e.g., dispersion of gaze or return of gaze) of the driver increased depending on the level of tension based on the stimulation (e.g., auditory stimulation) provided by the vehicle. The sensor device 11 may be put on the wrist of the driver or provided in a wearable device to be put on the head of the driver to sense the heart rate of the driver as illustrated in FIG. 6. In addition, the sensor device 11 may be provided in a steering wheel or a gear knob of the vehicle to sense the gaze information of the driver as illustrated in FIG. 7.

Referring back to FIG. 2, the controller 12 may allow the sensor device 11 to perform a sensing operation by receiving information from the vehicle 20.

The communication device 13 may transmit, to the vehicle 20, information sensed by the sensor device 11 of the measurement device 10 in a wired manner or a wireless manner. In addition, the communication device 13 may receive information from the vehicle 20.

The vehicle 20 may include a stimulation generator 21, a communication device 22, a signal processor 23, a learning device 24, a determiner 25, and a vehicle controller 26.

According to embodiments of the present disclosure, the stimulation generator 21 may be a device to provide auditory stimulation to the driver if the driver boards on the vehicle. For example, the auditory stimulation may be a welcome sound, a seat belt warning sound or a vehicle start sound. According to another example, if the driver is careless, the auditory stimulation may be a warning sound for carelessness. The stimulation generator 21 is not limited to devices which generate a sound for the auditory stimulation, but may include a device which generates a visible effect for visible stimulation.

The communication unit 22 may receive information sensed by the sensor device 11 of the measurement device 10 in a wired manner or a wireless manner and may transmit the received information to the learning device 24.

The signal processor 23 processes brainwave information sensed by the sensor device 11 of the measurement device 10.

In more detail, the signal processor 23 may include a filter 23-1, a down-sampler 23-2, and a feature point extractor 23-3.

The filter 23-1 may remove other frequency bands from the sensed brainwave information except meaningful frequency bands. Signals other than a brainwave signal may be treated as noise.

The down-sampler 23-2 may improve system efficiency by utilizing an electro encephalo-gram (EEG) time point.

The feature point extractor 23-3 may extract a meaningful ERP signal. For example, the feature point extractor 23-3 may extract a P300 potential component from the ERP and may use the P300 potential component as a reaction signal of the driver to the stimulation of the present disclosure. The details thereof will be described below with reference to FIG. 8.

Figure 8:
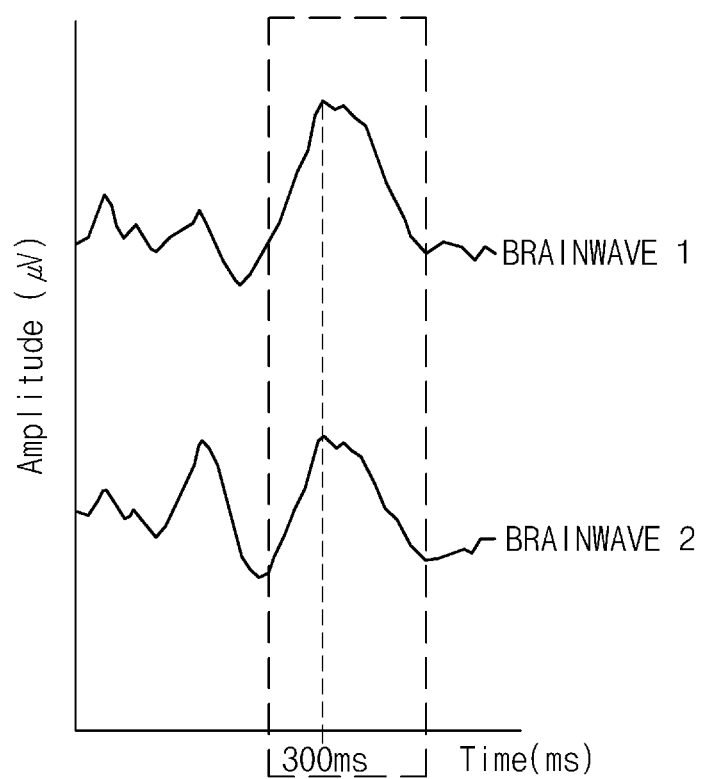
FIG. 8 is a graph illustrating the brainwave of the driver, which is used to adjust the driving control authority, according to embodiments of the present disclosure.

FIG. 8 is a graph illustrating the brainwave of the driver, which is used to adjust the driving control authority according to embodiments of the present disclosure.

The P300 potential component of the ERP in the above-described brainwave of the person is not the physical characteristic of the stimulation but is related to the reaction of the person. In detail, the P300 potential component has a feature of representing that the brainwave signal rises or increases after about 300 ms (a dotted rectangular part) if the normal reaction is made to the auditory stimulation signal. Accordingly, even P300 potential components of brainwave #1 and brainwave #2 may be measured in patterns as illustrated in the graph of FIG. 8.

Referring again to FIG. 2, the feature point extractor 23-3 may extract the P300 potential component from the reaction signal of the driver to stimulation (e.g., auditory stimulation) generated from the vehicle, for example, the auditory stimulation such as a welcome sound or a seat-belt warning sound.

The determiner 25 determines whether the driver is in a normal state or an abnormal state by analyzing a main signal pattern (i.e., feature point) extracted from the brainwave signal based on the driver state. The details thereof will be described below with reference to FIG. 9.

Figure 9:
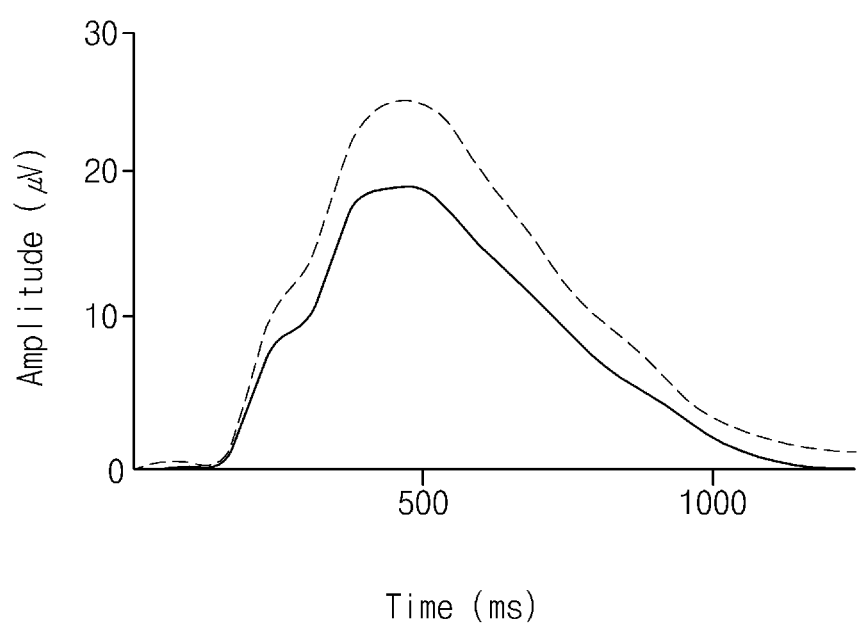
FIG. 9 is a graph illustrating the comparison between brainwave signals based on the driver state.

FIG. 9 is a graph illustrating the comparison between brainwave signals based on the driver state.

As illustrated in FIG. 9, the brainwave signal based on the driver state may be determined by using the maximum amplitudes of the brainwave signals. As described with reference to FIG. 8, the P300 potential component of the ERP has a feature of representing that the brainwave signal rises or increases after about 300 ms (a dotted rectangular part) if the normal reaction is made with respect to the auditory stimulation signal. Referring to FIG. 9 based on the above feature, it may be recognized that a dotted curve and a solid curve have the maximum amplitudes after about 300 ms from that the stimulation starts.

The dotted curve represents the brainwave signal of a driver in a normal state and the solid curve represents the brainwave signal of the driver in a drunken state. As described above, the brainwave signals of the driver in the normal state and the drunken state have the maximum amplitudes after about 300 ms from that the abnormal stimulation starts.

However, the brainwave signal of the driver in the drunken state is lower than the brainwave signal of the driver in the normal state in the maximum amplitude value. Accordingly, it may be understood that the driver is more insensitive to the stimulation from the outside in the abnormal state rather than the normal state. According to the present disclosure, for the convenience of explanation, if the maximum amplitude value is equal to or more than a reference value, it is assumed that the driver has the brainwave signal in the normal state. If the maximum amplitude value is less than the reference value, it is assumed that the driver has the brainwave signal in the abnormal state. Accordingly, as illustrated in FIG. 9, if the maximum amplitude value of the brainwave signal of the driver is equal to or more than the reference value, the determiner 25 determines the driver to be in the normal state. In addition, if the maximum amplitude value of the brainwave signal of the driver is less than the reference value, the determiner 25 determines the driver to be in the abnormal state.

Referring back to FIG. 2, the learning device 24 may learn information received from the determiner 25. The learning device 24 may learn the determination result of the determiner using feature points extracted from the feature point extractor 23-3 through support vector machine (SVM), linear discriminant analysis (LDA), or a neural network.

For example, if the maximum amplitude value of the extracted P300 potential is equal to or more than the reference value, learning is performed in that the driver state is the normal state. If the maximum amplitude value of the extracted P300 potential is less than the reference value, the learning is performed in that the driver state is the abnormal state.

If the driver state is determined to be the normal state based on the learning result, the vehicle controller 26 may control the vehicle to perform any one of autonomous driving or manual driving. However, if the driver state is determined to be the abnormal state, the vehicle controller 26 may control the vehicle to only autonomously drive instead of manual driving and may allow the driver to perform only the function related to movement to a destination. The vehicle controller 26 may control the vehicle to be switched into an emergency stop mode.

Figure 10:
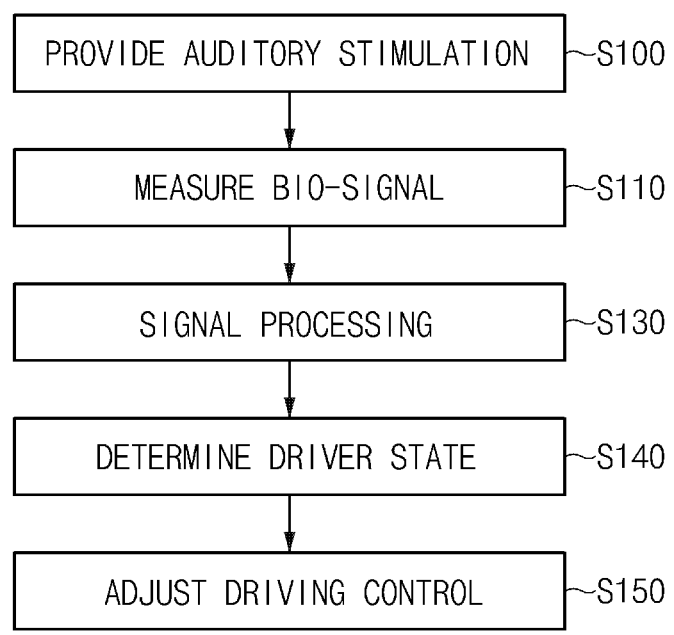
FIG. 10 is a flowchart illustrating a method for adjusting the driving control authority, according to embodiments of the present disclosure.

FIG. 10 is a flowchart illustrating a method for adjusting the driving control authority according to embodiments of the present disclosure.

As illustrated in FIG. 10, the vehicle controller 26 generates auditory stimulation to a driver if the driver boards the vehicle (S100). The auditory stimulation may include a welcome sound, a seat belt warning sound, or a vehicle start sound. In addition, the auditory stimulation may include a warning sound for carelessness of the driver.

The vehicle controller 26 measures the reaction signal of a driver to the auditory stimulation (S110). According to embodiments of the present disclosure, the reaction signal may be measured using the brainwave of the driver generated from the temporal lobe of the driver.

For reference, the brainwave of a person may be acquired from an ERP, an SSVEP, an ERS, an ERD, a default mode network, or the combination thereof.

In addition, according to another example, a bio-signal reacting to the auditory stimulation may be used. The bio-signal information may include a heart rate of a driver or the gaze information (e.g., dispersion of gaze or return of gaze) of the driver.

The vehicle controller 26 may perform signal processing for the reaction signal measured in operation S110 (S130). Operation S130 may include performing filtering to remove noise from a signal other than the brainwave, performing down-sampling to improve the system efficiency by utilizing an EEG time point, and extracting the ERP.

In more detail, in operation S130, a P300 potential component serving as a feature point may be extracted from the ERP and may be used as the reaction signal of the driver to the stimulation according to the present disclosure.

The P300 potential component of the ERP is not the physical characteristic of the stimulation but is related to the reaction of the person. In detail, the P300 potential component represents a pattern that the brainwave signal rises or increases after about 300 ms if the normal reaction is made to the auditory stimulation signal.

Referring again to FIG. 2, the feature point extractor 23-3 may extract and use the P300 potential component as the reaction signal of the driver to stimulation (auditory stimulation) generated from the vehicle, for example, the auditory stimulation such as a welcome sound or a seat-belt warning sound.

The vehicle controller 26 determines the driver state based on the signal processed in operation S130 (S140). If the maximum amplitude value of the signal (P300 potential) processed in operation S130 is greater than or equal to a reference value, the vehicle controller 26 determines the driver to be in the normal state. If the maximum amplitude value of the signal (P300 potential) processed in operation S130 is less than a reference value, the vehicle controller 26 determines the driver to be in the abnormal state The vehicle controller 26 adjusts the driving control authority based on the determination result in operation S140 (S150). If the driver state is determined to be the normal state, the vehicle controller 26 may adjust the driving control authority of the vehicle to perform any one of autonomous driving and manual driving. However, if the driver state is determined to be the abnormal state, the vehicle controller 26 may control operation of the vehicle such that the vehicle only performs autonomously driving instead of manual driving and may control the vehicle such that only the function related to movement to a destination is operated. The vehicle controller may also control the vehicle to be switched into an emergency stop mode.

According to embodiments of the present disclosure, an emergency situation may occur to a driver while the driver personally drives a vehicle with driving control authority over the vehicle. For example, in the case that the driver is drowsy, the emergency situation of the driver is recognized by the sensor of the vehicle and an alarm sound is sent to the driver. However, even though the alarm sound is sent to the driver, the driver may not perceive the alarm sound due to extreme drowsiness. In this case, the vehicle controller 26 forcibly deprives the driver of the driving control authority to prevent the driver from being involved in driving the vehicle and allows the system to have the driving control authority such that the vehicle autonomously drives.

According to another example, the vehicle controller 26 recognizes, in an initial stage, whether the driver perceives a welcome sound of the vehicle, a vehicle state check sound, or a seat belt warning sound of the vehicle generated when the driver boards the vehicle, and allows the vehicle to drive in any one of an autonomous driving mode and a manual driving mode. When the vehicle enters the autonomous driving mode, the vehicle generates visible stimulation or auditory stimulation, and measures the reaction to the simulation. If the driver is determined in the normal state based on the reaction result to the stimulation, the vehicle may be switched into the manual driving mode. However, if the driver is determined in the abnormal state, the vehicle may be maintained in the autonomous driving mode instead of being switched into the manual driving mode.

According to another example, the vehicle may perform a function of measuring or determining the reaction of the driver to an alarm sound generated when the driver drives the vehicle carelessly. If the driver is determined to less perceive the alarm sound generated when the driver drives the vehicle carelessly, an autonomous driving function may be automatically (forcibly) activated. In addition, if the driver is determined to, to a lower extent, perceive the alarm sound generated when the driver drives the vehicle carelessly, a surrounding road environment is determined. If the surrounding road environment is determined to be safe, an emergency shoulder parking function and an emergency braking function may be activated. Accordingly, safety accident may be prevented from being caused due to the careless driving.

Figure 11:
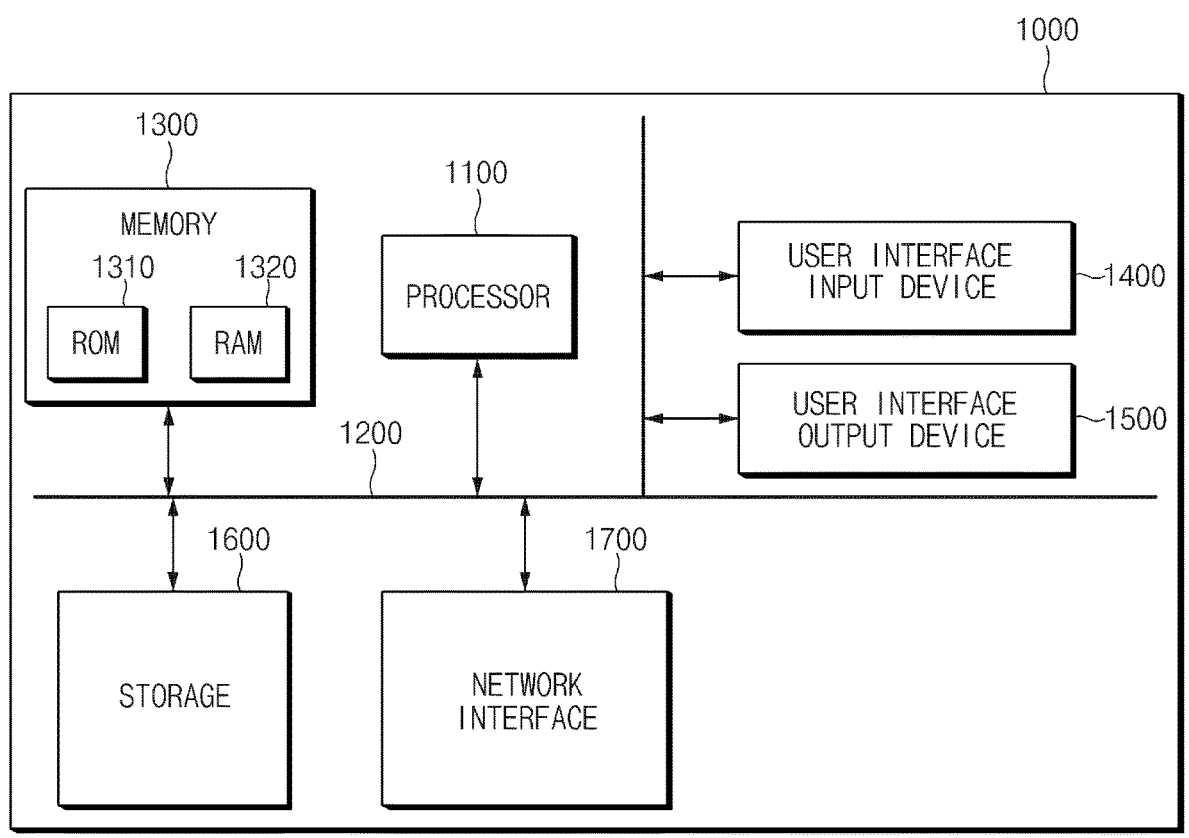
FIG. 11 is a block diagram illustrating a computing system to execute the method, according to embodiments of the present disclosure.

FIG. 11 is a block diagram illustrating a computing system to execute the method according to embodiments of the present disclosure.

As illustrated in FIG. 11, a computing system 1000 may include at least one processor 1100, a memory 1300, a user interface input device 1400, a user interface output device 1500, a storage 1600, and a network interface 1700, which are connected with each other via a bus 1200.

The processor 1100 may be a central processing device (CPU) or a semiconductor device for processing instructions stored in the memory 1300 and/or the storage 1600. Each of the memory 1300 and the storage 1600 may include various types of volatile or non-volatile storage media. For example, the memory 1300 may include a read only memory (ROM) and a random access memory (RAM).

Thus, the operations of the methods or algorithms described in connection with the embodiments disclosed in the present disclosure may be directly implemented with a hardware module, a software module, or the combinations thereof, executed by the processor 1100. The software module may reside on a storage medium (i.e., the memory 1300 and/or the storage 1600), such as a RAM, a flash memory, a ROM, an erasable and programmable ROM (EPROM), an electrically EPROM (EEPROM), a register, a hard disc, a removable disc, or a compact disc-ROM (CD-ROM). The exemplary storage medium may be coupled to the processor 1100. The processor 1100 may read out information from the storage medium and may write information in the storage medium. Alternatively, the storage medium may be integrated with the processor 1100. The processor and storage medium may reside in an application specific integrated circuit (ASIC). The ASIC may reside in a user terminal. Alternatively, the processor and storage medium may reside as separate components of the user terminal.

As described above, in the state that the driver does not personally control the driving of the vehicle, an assist function for the vehicle driving is automatically activated or the driving control authority is forcibly recovered from the driver, thereby preventing a safety accident.

Hereinabove, although the present disclosure has been described with reference to certain embodiments and the accompanying drawings, the present disclosure is not limited thereto, but may be variously modified and altered by those skilled in the art to which the present disclosure pertains without departing from the concept and scope of the present disclosure claimed in the following claims.

Therefore, embodiments of the present disclosure are not intended to limit the technical concept of the present disclosure, but provided only for the illustrative purpose. The scope of protection of the present disclosure should be construed by the attached claims, and all equivalents thereof should be construed as being included within the scope of the present disclosure.

What is claimed is:

1. A method for adjusting a driving control authority of a vehicle, the method comprising:
   generating stimulation including sound generated when a driver boards the vehicle for a driver using a stimulation generator, wherein the sound includes a welcome sound or a seat belt warning sound;
   measuring a driver reaction signal in response to the generated stimulation using a measurement device, wherein the driver reaction signal comprises measuring a brainwave of the driver;
   processing the measured driver reaction signal using a signal processor;
   determining a driver state based on the processed driver reaction signal using a processor; and
   adjusting the driving control authority of the vehicle according to the determined driver state using a vehicle controller,
   wherein the processing of the driver reaction signal comprises:

performing filtering on the driver reaction signal to classify a signal other than the brainwave as noise;
extracting an event-related potential (ERP) from the filtered driver reaction signal; and
extracting, from the ERP, a potential having a maximum amplitude value after a specific time elapses from a time at which the stimulation is generated.

2. The method of claim 1, wherein the measuring of the driver reaction signal comprises:
measuring a bio-signal of the driver.

3. The method of claim 2, wherein the measuring of the driver reaction signal further comprises:
measuring one of a heart rate of the driver and gaze information of the driver.

4. The method of claim 3, wherein the determining of the driver state comprises:
determining the driver state to be a normal state when the maximum amplitude value of the brainwave is greater than or equal to a reference value.

5. The method of claim 4, wherein the adjusting of the driving control authority of the vehicle comprises:
controlling operation of the vehicle such that the vehicle performs either autonomous driving or manual driving when the driver state is the normal state.

6. The method of claim 3, wherein the determining of the driver state comprises:
determining the driver state to be an abnormal state when the maximum amplitude value of the brainwave is less than a reference value.

7. The method of claim 6, wherein the adjusting of the driving control authority of the vehicle comprises:
controlling operation of the vehicle such that the vehicle performs either autonomous driving or an emergency stop when the driver state is the abnormal state.

8. A system for adjusting a driving control authority of a vehicle, the system comprising:
a stimulation generator to generate stimulation for a driver, wherein the stimulation including sound generated when a driver boards the vehicle, wherein the sound includes a welcome sound or a seat belt warning sound;
a measurement device including a sensor device configured to measure a driver reaction signal in response to the generated stimulation;
a signal processor configured to:
process the measured driver reaction signal, wherein the driver reaction signal comprises measuring a brainwave of the driver;
perform filtering on the driver reaction signal to classify a signal other than the brainwave as noise;
extract an event-related potential (ERP) from the filtered driver reaction signal; and
extract, from the ERP, a potential having a maximum amplitude value after a specific time elapses from a time at which the stimulation is generated;
a processor configured to determine a driver state based on the processed driver reaction signal; and
a vehicle controller configured to adjust the driving control authority of the vehicle according to the determined driver state.

9. The system of claim 8, wherein the sensor device is included in the vehicle or wearable by the driver.

10. The system of claim 8, wherein the processor determines the driver state to be a normal state when the maximum amplitude value of the brainwave is greater than or equal to a reference value.

11. The system of claim 10, wherein the vehicle controller controls operation of the vehicle such that the vehicle performs autonomous driving or manual driving when the driver state is the normal state.

12. The system of claim 8, wherein the processor determines the driver state to be an abnormal state when the maximum amplitude value of the brainwave is less than a reference value.

13. The system of claim 12, wherein the vehicle controller controls operation of the vehicle such that the vehicle performs either autonomous driving or an emergency stop when the driver state is the abnormal state.

* * * * *